United States Patent [19]
Gould et al.

[11] Patent Number: 4,586,923
[45] Date of Patent: May 6, 1986

[54] CURVING TIP CATHETER

[75] Inventors: Sheldon D. Gould, North Miami; Gary T. Riggs, West Palm Beach, both of Fla.

[73] Assignee: Cordis Corporation, Miami, Fla.

[21] Appl. No.: 624,007

[22] Filed: Jun. 25, 1984

[51] Int. Cl.[4] .............................................. A61M 25/00
[52] U.S. Cl. ....................................... 604/95; 128/657
[58] Field of Search ............................. 128/656-658, 128/772, 4, 8; 604/95, 170

[56] References Cited

U.S. PATENT DOCUMENTS

| 1,913,229 | 6/1933 | Bordier . | |
|---|---|---|---|
| 2,688,329 | 9/1954 | Wallace | 604/95 |
| 3,416,531 | 12/1968 | Edwards | 128/348 |
| 3,452,740 | 7/1969 | Muller | 128/2 |
| 3,452,742 | 7/1969 | Muller | 128/2 |
| 3,470,876 | 10/1969 | Barchilon | 604/95 |
| 3,485,234 | 12/1969 | Stevens | 128/2 |
| 3,500,820 | 3/1970 | Almen | 128/2 |
| 3,521,620 | 7/1970 | Cook | 128/2.05 |
| 3,547,103 | 12/1970 | Cook | 128/2.05 |
| 3,552,384 | 1/1971 | Pierie et al. | 128/2.05 |
| 3,605,725 | 9/1971 | Bentov | 128/2.05 R |
| 3,773,034 | 11/1973 | Burns et al. | 128/2 M |
| 3,854,473 | 12/1974 | Matsuo | 128/8 |
| 3,924,632 | 12/1975 | Cook | 128/348 |
| 4,020,829 | 5/1977 | Willson et al. | 128/2 M |
| 4,033,331 | 7/1977 | Guss et al. | 128/2 M |
| 4,245,624 | 1/1981 | Komiya | 128/4 |

FOREIGN PATENT DOCUMENTS

| 1213571 | 3/1966 | Fed. Rep. of Germany | 604/95 |
|---|---|---|---|
| 43-27695 | 11/1968 | Japan . | |
| 43-27659 | 11/1968 | Japan | 604/95 |
| 548462 | 10/1942 | United Kingdom | 128/8 |

Primary Examiner—Dalton L. Truluck
Attorney, Agent, or Firm—Henry W. Collins; Thomas R. Vigil

[57] ABSTRACT

The curving tip catheter is adapted to be inserted into and through the lumen of a blood vessel in a network of branching blood vessels in a body and is manipulatable therethrough to a desired blood vessel branch within the network of branching blood vessels. The catheter includes an elongate tubular body having a distal end and a proximal end, and a flexible tubular tip portion located at the distal end of the elongate tubular body. The catheter further includes at least first and second elongate passageways within the tubular body and at least first and second elongate lumens within the flexible tip portion and which mate with the first and second respective elongate passageways of the tubular body. The tubular body includes braided wire embedded into the wall of the tubular body, or an inner tubular lining within the tubular body situated between the tubular body and the first and second elongate passageways, both of which provide torsional stiffness to the tubular body. A wire is situated within the first passageway of the tubular body and the first lumen of the flexible tip portion and which is coupled to the distal end of the flexible tip portion and the wire having its proximal end connected to a mechanism for pulling the wire in order to cause the tip member to bend or flex accordingly.

The catheter further includes a mechanism located at the proximal end of the catheter for introducing or withdrawing a fluid material into or from the second passageway in the tubular body whereby the catheter can be guided by bending the flexible tip member through a branching network of blood vessels of a body to a site in the body for delivering the fluid or withdrawing the fluid from the site in the body.

19 Claims, 7 Drawing Figures

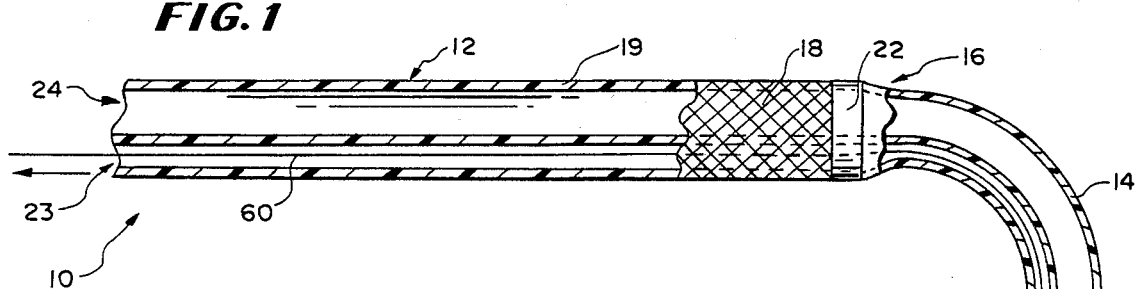
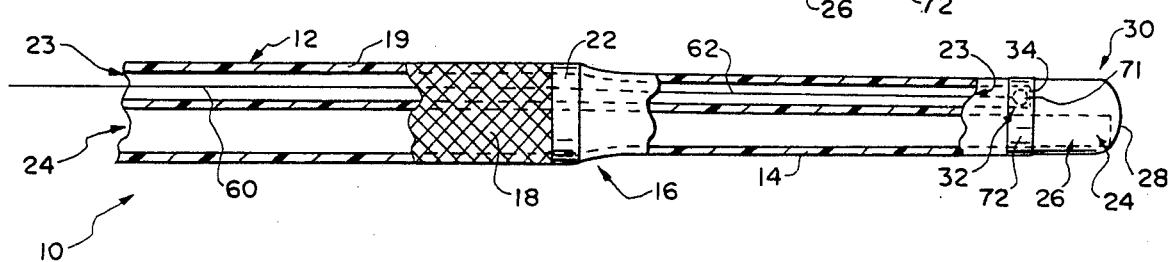
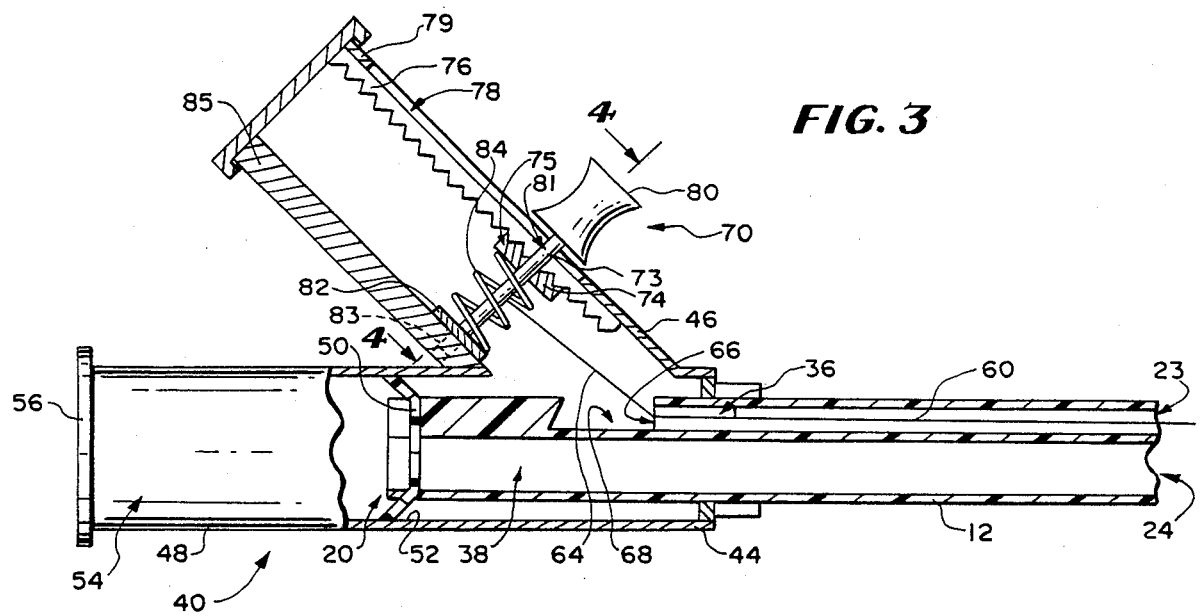
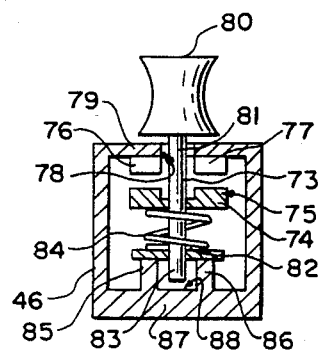

CURVING TIP CATHETER

BACKGROUND OF THE INVENTION

1. Field of the Invention

The present invention relates to a curving tip catheter that is inserted into and through the lumen of a blood vessel in a network of branching blood vessels of a body and which is adapted to be manipulated therethrough to a selected blood vessel branch within the network of branching blood vessels and which is further adapted to deliver or withdraw a fluid material to or from the selected vessel branch within the network of blood vessels.

The catheter of the present invention includes an elongate tubular body and a flexible tubular tip portion at the distal end of the tubular body. The catheter further includes a control mechanism located at the proximal end of the catheter which is coupled to the flexible tip portion of the tubular body. The control mechanism is adapted to bend or flex the flexible tip portion relative to the plane of the tubular body of the catheter in order that the flexible tip portion can guide the catheter to and through a selected vessel branch of a branching network of blood vessels of the body.

2. Description of the Prior Art

Heretofore, various catheters have been proposed which include bending or flexing tip members or other mechanisms attached thereto for guiding a catheter through branching vessels of a body. Examples of such previously proposed catheters are disclosed in the following U.S. patents and in the following Japanese patent publication:

| U.S. PAT. NO. | PATENTEE |
| --- | --- |
| 1,913,229 | Bordier |
| 3,416,531 | Edwards |
| 3,452,740 | Muller |
| 3,452,742 | Muller |
| 3,470,876 | Barchilon |
| 3,500,820 | Almen |
| 3,521,620 | Cook |
| 3,547,103 | Cook |
| 3,552,384 | Pierie et al |
| 3,605,725 | Bentov |
| 3,773,034 | Burns et al |
| 4,033,331 | Guss et al |
| 4,245,624 | Komiya |

Senzo Japanese Patent Publication No. 43-27695

The Bordier U.S. Pat. No. 1,913,229 discloses an aspirating instrument adapted to be used in connection with aspirating devices which are used in medical and surgical practices. The aspirating instrument includes a body having two passageways formed therethrough and a flexible rod located within one of the passageways. The flexible rod carries an index flag which is adapted to indicate the position of the tip of the flexible rod when it is inserted into a cavity which is to be emptied of a liquid. The body of the instrument is first introduced into the cavity with the tip of the flexible rod extending beyond the distal end of the body and serving as a guide into the cavity to be evacuated.

The Edwards U.S. Pat. No. 3,416,531 discloses a catheter tube reinforced with braided wire and which includes a longitudinal passageway therethrough and which is adapted to be connected to a manipulatable handle. The manipulatable handle includes a flexible guide tube which is insertable into the catheter tube and includes a pull wire which is coupled to and controlled by the manipulatable handle and which can be inserted into the longitudinal passageway of the catheter tube. A bending element is located at the distal end of the pull wire and is insertable into the longitudinal passageway of the catheter tube. When the manipulatable handle to which the catheter tube is attached is rotated, the rotation of the handle causes the catheter tube, the guide tube, the pull wire and the bending element to rotate accordingly. The rotation of the handle further causes the frictional engagement of the bending element with the inside of the catheter tube so that the end or tip of the catheter tube bends when the wire is pulled by the manipulatable handle in order to guide the tip of the catheter into a branching artery.

The Muller U.S. Pat. No. 3,452,740 discloses a spring guide manipulator having a handle for attachment to and manipulation of a spring guide which is used to guide a catheter to specific locations within the circulatory system. The spring guide is formed from a continuous wire coil and includes a tensioning wire which extends therethrough. The distal end of the spring guide is closed by a catheter plug and the proximal end of the spring guide is connected to a front chuck in the manipulatable handle. The distal end of the wire is connected to the plug, and the proximal end of the wire is connected to a back chuck which is located behind the front chuck. When the manipulatable handle is connected to the proximal end of the spring guide and tension is applied to the tensioning wire by moving the back chuck axially away from the front chuck, the wire is axially displaced in order to flex the distal end of the spring guide.

The Muller U.S. Pat. No. 3,452,742 discloses a controllable vascular curvable spring guide comprising a wire coil and a core wire within the wire coil wherein the distal end of the core wire is permanently secured to the distal end of the wire coil by a cap. The arcuate portions of the individual coils of the spring guide along the inner radius of the spring guide have a decreased diameter relative to the increased diameter of their arcuate portions along the outer radius of the spring guide so that when a pulling force is applied to the wire toward the proximal end of the core wire, the distal tip of the spring guide will curve or bend toward the inner radius of the spring guide.

The Barchilon U.S. Pat. No. 3,470,876 discloses a dirigible catheter which includes an outer cylindrical wall member which is continuous along the length of the catheter and an inner catheter tube situated within the outer cylindrical wall member. An end piece having a flange is mounted around the distal end of the inner catheter tube. The flange receives four guiding or tensioning cords which are fastened to the flange and which extend through tube-like members within the catheter body. Accordingly, selective tensioning of one of the four tensioning cords will direct the distal end of the catheter in any direction throughout 360° with respect to a plane perpendicular to the axis thereof. The catheter is further adapted to be mounted to a manipulatable device which contains a mechanism for selectively operating each of the tensioning cords.

The Almen U.S. Pat. No. 3,500,820 discloses a medical probe for injecting contrast medium into the body and which includes an outer hose, a flexible tube inserted within the hose which is slidably movable therein, and a bending element inserted in the tube and which is also slidably movable therein. The bending element consists of two relatively thin narrow wires having a rectangular cross-section and which have their distal ends soldered together and which extend through the distal end of the flexible inner tube. The proximal ends of the wires are connected to the handle and are movable back and forth in relation to each other and to the flexible tube so that when the wires are lengthened or shortened in relation to each other the distal end of the catheter is curved by the axial displacement of the wires of the bending element.

The Cook U.S. Pat. No. 3,521,620 discloses a vascular coil spring guide with a bendable tip which includes a coil spring and a wire extending within the coil spring which has its distal end attached to a tip member located at the distal end of the coil spring. The coil spring guide further includes a flat wire secured to the tip member of the coil spring and which occupies a small portion of the distal end of the coil spring. The flat wire is positioned adjacent or in engagement with the inside surface of the coil spring on one side of the coil spring and opposite the wire. The wire moves freely within the coil spring and its proximal end is connected to a controlling and holding tool located at the proximal end of the coil spring. When the wire is pulled or thereby manipulated by the controlling and holding tool, the distal end of the coil spring will bend in a direction opposite the side of the coil spring to which the flat wire is secured as a result of the rigidity provided by the flat wire to the side of the coil spring to which the flat wire is attached.

The Cook U.S. Pat. No. 3,547,103 discloses a coil spring guide having a mandrel therein extending from the proximal end of the spring guide toward and into the distal end of the spring guide. A wire also extends through the coil spring guide and extends beyond the distal end of the mandrel and is attached to a tip member located at the distal end of the spring guide. The coil spring and the wire are curved at the distal end of the spring guide so that the coil spring defines a J-shape so that when the proximal end of the spring guide is held with one hand and pulled with another hand, the wire is also pulled with the result that the distal end of the spring guide is straightened.

The Pierie et al U.S. Pat. No. 3,552,384 discloses a controllable tip guide body and catheter wherein the guide body comprises a flexible plastic tube having a flexible pull wire extending therethrough and attached to the distal end of the guide body so that when the pull wire is manipulated or pulled, the distal end of the guide body will bend.

The Bentov U.S. Pat. No. 3,605,725 discloses a controlled motion device which comprises a catheter body having a frusto-conical metal insert located at and within its distal end into which are mounted three flexible control wires positioned 120° apart. The control wires extend rearwardly through passageways in the catheter body to a control housing located at the proximal end of the catheter body. The control housing includes a Y-shaped tube which communicates with a central passageway through the catheter body so that a stiff guide wire can be inserted through one of the arms of the Y-shaped tube and into the central passageway in order to facilitate insertion of a catheter into a blood vessel. When the guide wire is positioned into the distal end of the catheter, it stiffens a predetermined portion of the distal end of the catheter within which the guide wire occupies and permits the remaining portion of the distal end of the catheter which is unoccupied by the guide wire to flex by manipulation of the control wires by the control housing.

The Burns et al U.S. Pat. No. 3,773,034 discloses a steerable catheter which includes an elongate flexible tubular member having one or more passageways therethrough and a steerable fluid control apparatus connected to the proximal end of the tubular member. Bending of the distal end of the tubular member is controlled by a fluid force which is introduced by the fluid control apparatus into and through the passageways.

The Guss et al U.S. Pat. No. 4,033,331 discloses a cardiac catheter formed with a main lumen and a wire lumen extending throughout the length of the catheter wherein the main lumen is open from its proximal end through an opening at the distal end of the catheter, while the wire lumen is open from the proximal end of the catheter and is closed at the distal end of the catheter. The catheter is flexible throughout its length and has a deformable, preformed distal end that is formed with a set curvature so that when a stiffening wire, which slidably resides within the wire lumen, is removed, the distal end of the catheter will resume its preformed or sharply formed curved tip.

The Komiya U.S. Pat. No. 4,245,624 discloses an endoscope with a flexible tip control and which includes a tube section having first and second channels or passageways therethrough, a cylindrical guide tube slidably inserted through the first channel, and a slidable wire inserted through the second channel. The distal end of the wire is fixed to the outer wall of the guide tube at the distal end of the guide tube, and the other end of the wire extends through the tube section to a control section which is connected to the proximal end of the tube section. When the guide tube and the wire are made to move forward by the control section so that both the guide tube and the wire are simultaneously pushed out of the distal end of the tube section, the wire is then pulled toward the control section so that the flexible distal end of the guide tube is thereby bent.

The Senzo Japanese Patent Publication No. 43-27695 discloses a catheter which includes a tubular core which comprises a coiled helical wire and a control wire extending therethrough having its distal end welded to the distal end of the coiled wire, and the proximal end of wire connected to a control knob for manipulating the wire. When the wire is pulled by manipulating the control knob, the coiled end portion of the coiled helical wire is caused to reduce its interwiring spacing at the pulled side of the coiled wire to which the control wire is attached, thereby causing the distal end of the tubular core to bend in an arcuate form.

As will be described in greater detail hereinafter, the curving tip catheter of the present invention differs from the various catheters previously proposed by providing a catheter comprising a reinforced elongate tubular body having two separate passageways and having a distal end tip portion which is not reinforced so that the tip portion is flexible relative the reinforced tubular body. A pull wire slidably extends through one of the elongate passageways. A distal end of the pull wire is connected to the flexible tip portion, and a proximal end of the pull wire is connected to a control mechanism mounted to the proximal end of the tubular body. The control mechanism is adapted to be manipulated to bend the flexibility portion relative to the tubular body in a rearward direction toward the control housing in order to permit the catheter to be guided by the flexible tip portion into a selected blood vessel branch in a network of branching blood vessels.

SUMMARY OF THE INVENTION

According to the present invention, there is provided a catheter adapted to be inserted into and through the lumen of a blood vessel in a network of branching blood vessels of a body and which is manipulatable therethrough to a desired blood vessel branch within the network of branching blood vessels. The catheter comprises an elongate tubular body having a distal end and a proximal end and a flexible tubular tip portion located at the distal end of the elongate tubular body. The tubular body includes at least first and second elongate passageways within the tubular body. The flexible tip portion includes at least first and second elongate lumens within the flexible tip portion and mating with the first and second respective elongate passageways within the tubular body. The tubular body is reinforced to provide torsional stiffness to the tubular body. A cable is situated within the first passageway and the first lumen and is coupled to the flexible tip portion for flexing the flexible tip portion. A mechanism is coupled to the tubular body for introducing or withdrawing fluid material into or from the second passageway in the tubular body. Another mechanism is coupled to the cable for manipulating same whereby the catheter can be guided by the flexible tip portion through a branching network of blood vessels in a body to a site in the body for delivering a fluid or withdrawing a fluid from the site in the body.

BRIEF DESCRIPTION OF THE DRAWINGS

FIG. 1 is a longitudinal sectional view of a curving tip catheter constructed according to the teachings of the present invention and shows a flexible tip portion of the catheter in its bent or curved position.

FIG. 2 is a longitudinal sectional view of the curving tip catheter and shows the flexible tip portion of the catheter in its normal, straight position.

FIG. 3 is a longitudinal sectional view of one embodiment of a control mechanism constructed according to the teachings of the present invention and which is adapted to bend the flexible tip portion of the catheter.

FIG. 4 is a sectional view taken along line 4—4 of FIG. 3.

DESCRIPTION OF THE PREFERRED EMBODIMENTS

Figure 5:
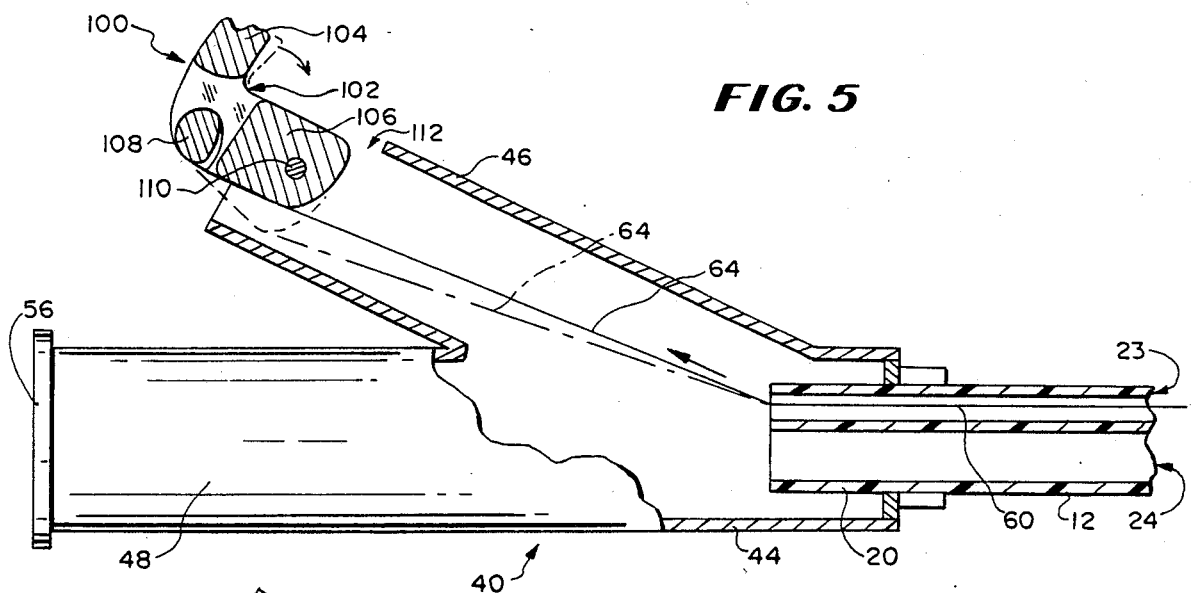
FIG. 5 is a longitudinal sectional view of a second embodiment of the control mechanism of the present invention and which is adapted to bend the flexible tip portion of the catheter.

Referring now to FIG. 1, there is illustrated therein a curving tip catheter constructed according to the teachings of the present invention and generally identified by reference numeral 10. The catheter 10 is adapted to be inserted into and through the lumen of a selected blood vessel branch in a network of branching blood vessels to a desired site in a body for delivering a fluid to and/or withdrawing fluid from, the site in the body.

The catheter 10 includes an elongate tubular body 12 having a flexible tip portion 14 mounted to a distal end 16 of the tubular body 12. The tubular body 12 and the flexible tip portion 14 are formed from a flexible material, such as polyethylene, which is suitable for intravascular use and which provides maximum flexibility to permit manipulation of the catheter 10 through a blood vessel to a desired position therein within the blood vessel.

When the tubular body 12 and the flexible tip portion 14 are formed, a sheath of braided wire 18 having a mesh-like configuration is positioned around a wall 19 of the tubular body 12 from a proximal end 20 (FIG. 3) of the tubular body 12 to a first metal band 22. The first metal band 22 is wrapped around the distal end 16 of the tubular body 12 between the tubular body 12 and the flexible tip portion 14 to provide torsional stiffness to the tubular body 12 relative to the flexible tip portion 14. In the alternative, a relatively stiff but bendable inner plastic tubular lining (not shown) can be inserted within the tubular body 12 in order to provide torsional stiffness to the tubular body 12.

The catheter 10 further includes first and second elongate passageways 23,24 which extend within the tubular body 12 and within the flexible tip portion 14. The first elongate passageway 23 has a diameter which is approximately ⅓ the diameter of the second elongate passageway 24. A distal end 26 of the second elongate passageway 24 communicates with an opening 28 at a distal end 30 of the flexible tip portion 14 of the tubular body 12, and a distal end 32 of the first elongate passageway 23 terminates at an end wall 34, a short distance from the distal end 30 of the flexible tip portion 14 and within the flexible tip portion 14.

Referring now to FIG. 3, respective proximal ends 36,38 of the first and second elongate passageways 23,24 communicate with a Y or trident housing 40 which is located at the proximal end 20 of the tubular body 12 and which includes a leg portion 44, a first arm 46 and a second arm 48. The proximal end 20 of the tubular body 12 terminates within the second arm 48 of the trident housing 40 and is mounted or otherwise secured thereto by a fluid tight frusto-conical flange 50 which is located at, and mounted around the proximal end 20 of the tubular body 12 and mounted to an inner surface 52 of the second arm 48 of the trident housing 40. A proximal end 54 of the second arm 48 of the trident housing 40 includes a Luer connector 56 for connecting a syringe (not shown) or other device thereto for introducing a fluid material into the second arm 48 of the trident housing 40 and through the second elongate passageway 24 of the tubular body 12 and the flexible tip portion 14. The fluid material which is introduced into the second arm 48 of the trident housing 40 exits the flexible tip portion 14 through the opening 28 at the distal end 30 of the flexible tip portion 14. Alternatively, the syringe (not shown) can be used for the withdrawal of fluid material from the body through the second elongate passageway 24 of the flexible tip portion 14 and the tubular body 12.

As shown in the figures, an elongate pull wire 60 having a distal end 62 and a proximal end 64 is slidably situated within the first elongate passageway 23. The proximal end 64 of the wire 60 exits the first elongate passageway 23 through a proximal opening 66 of the first elongate passageway 23 and enters the first arm 46 of the trident housing 40 through an opening 68 in the proximal end 20 of the tubular body 12 and is coupled to a ratchet assembly 70.

The distal end 62 of the pull wire 60 is coupled to a second metal band 72 (FIGS. 1 and 2) which is wrapped around the distal end 30 of the flexible tip portion 14 of the tubular body 12. The distal end 62 of the pull wire 60 exits the flexible tip portion 14 through a hole 71 in the distal end 30 of the flexible tip portion 14, the hole 71 being located beneath the metal band 72. The distal end 62 is soldered or otherwise attached to the metal band 72.

The ratchet assembly 70 (FIG. 4), which is located in the first arm 46 of the trident housing 40, includes a pin 73 which is spring biased outwardly and transversely of the axis of the first arm 46. A first washer 74 is secured to the pin 73 and includes a plurality of stepped portions 75, which are engagable with two racks of gear plates 76, 77 positioned within the hollow first arm 46 on each side of an elongate axially extending slot 78 in the first arm 46. The racks 76 and 77 extend parallel to the axis of the first arm 46. The elongate axially extending slot 78 is located in an upper wall 79 of the first arm 46 of the trident housing 40. The pin 73 extends through the slot 78 and has the first washer 74 thereon positioned on the inner side of the wall 79 and a knob 80 connected to distal end 81 of the pin 73 on the outer side of the wall 79.

A second washer 82 is also located on a proximal end 83 of the pin 73 within the hollow first arm 46 and is positioned in a spaced apart relationship with respect to the first washer 74 and a spring 84 is located between the washers 74 and 82 on the pin 73. The second washer 82 is freely mounted on the pin 73 so that the pin 73 is movable relative to the washer 82 and the washer 74 moves with the pin 73 when the pin 73 is pushed inwardly by the knob 80 relative to the first arm 46 of the trident housing 40. The movable second washer 82 is adjacent to and rests upon two, spaced apart elongate ribs 85, 86 fixed on a lower wall 87 of the first arm 46 of the trident housing 40. The two ribs 85, 86 are perpendicular to and extend axially of the lower wall 87 of the first arm 46 and define a channel 88 therebetween.

The proximal end 64 of the pull wire 60 is connected to the pin 73 and the pin 73 includes a proximal end portion 83 which is received into the channel 88. The movable second washer 82 permits the pin 73 to slide through the second washer 82 upon compression of the spring 84 when the pin 73 is pushed inwardly by the knob 80. In this manner, the proximal end 83 of the pin 73 extends into the channel 88 and slides freely therethrough when the pin 73 is moved axially and radially of the axis of the first arm 46 so that the stepped portions 75 of the first washer 74 can be disengaged from the racks 76, 77. The slot 78 permits movement of the pin 73 axially and radially of the axis of the first arm 46 so that once the stepped portions 75 of the first washer 74 have been disengaged from the racks 76, 77, the pin 73 can be moved freely through the slot 78 in order to reengage the stepped portions 75 of the washer 74 with the racks 76, 77 at another position axially of the racks 76, 77 when the knob 80 is released.

It will be apparent that when the ratchet assembly 70 is moved in a rearward direction away from the tubular body 14, the pull wire 60 is pulled and freely slides through the first elongate passageway 23. The tension created on the pull wire 60 causes the flexible tip portion 14 of the tubular body 12 to bend in a direction toward the proximal end 20 of the tubular body 12 as shown in FIG. 1.

Then, when the ratchet assembly 70 is moved in a forward direction toward the tubular body 12, the tension on the pull wire 60 decreases and allows the flexible tip portion 14 to assume its normal, straight configuration as shown in FIG. 2.

It is to be understood that according to the teachings of the present invention, the flexible tip portion 14 of the tubular body 12 will always bend with the first elongage passageway 23 to the innermost radius or on the inside of the curving flexible tip portion 14.

It is also to be understood that according to the teachings of the present invention, the flexible tip portion 14 is permitted to bend relative to the tubular body 12 because of the braided wire reinforcement 18 in the tubular body 12 as well as the added reinforcement which is provided by the first metal band 22 located between the distal end 16 of the tubular body 12 and the flexible tip portion 14.

The flexible tip portion 14 is then caused to bend by manipulation of the pull wire 60 by the ratchet assembly 70 while, at the same time, the tubular body 12 remains relatively rigid up to the first metal band 22.

Figure 6:
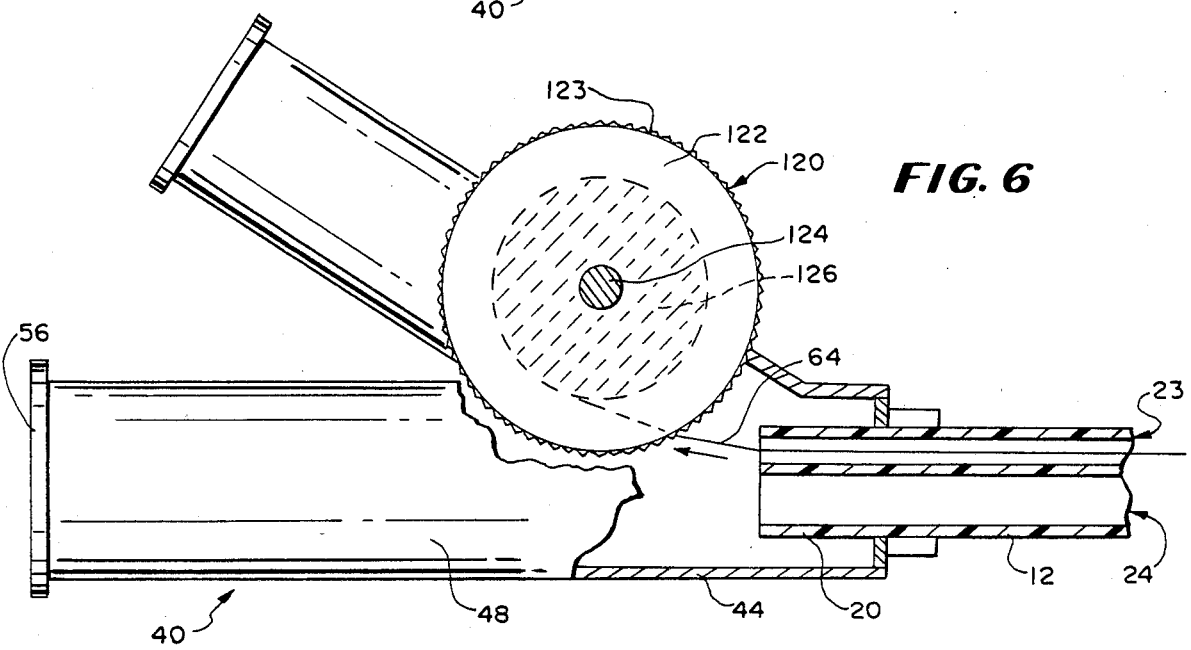
FIG. 6 is a longitudinal sectional view of a third embodiment of the control mechanism of the present invention and which is adapted to bend the flexible tip portion of the catheter.
Figure 7:
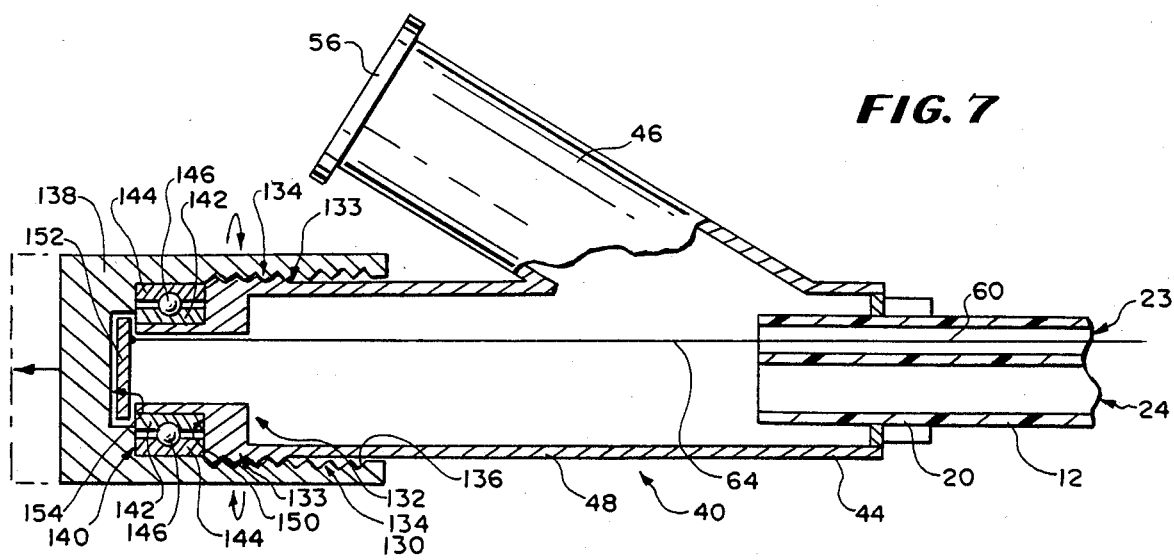
FIG. 7 is a longitudinal sectional view of a fourth embodiment of the control mechanism of the present invention and which is adapted to bend the flexible tip portion of the catheter.

FIGS. 5–7 illustrate other mechanisms for manipulating the pull wire 60 in order to control the bending or flexing of the flexible tip portion 14.

For example, a lever assembly 100 for manipulating pull wire 60 is shown in FIG. 5. The proximal end 64 of the pull wire 60 is connected to the lever assembly 100 as shown. The lever assembly 100 includes a lever 102 which has an L-shaped configuration, a first arm 104, a second arm 106, and an elbow portion 108 therebetween. The second arm 106 of the lever 102 is positioned within the first arm 46 of the trident housing 40 and is pivotable therein about a pivot shaft 110 which has each of its ends pivotably mounted to the first arm 46 of the trident housing 40. The proximal end 64 of the pull wire 60 is attached to the elbow 108 of the lever 102 so that when the first arm 104 of the lever 102 is moved in a forward direction toward the tubular body 12 through a slit 112 in the first arm 46 of the trident housing 40 (shown in phantom in FIG. 5) the pull wire 60 is pulled by the elbow 108 of the lever 102 so that the flexible tip portion 14 of the tubular body 12 bends in a rearward direction toward the trident housing 40. When the lever 102 is returned to the position shown in FIG. 5, the pull wire 60 slides in a forward direction toward the flexible tip portion 14 and permits the flexible tip portion 14 of the tubular body 12 to return to its normal, straight configuration shown in FIG. 2.

In another embodiment, a wheel assembly 120 is provided for manipulating the pull wire 60 as shown in FIG. 6. The wheel assembly 120 includes a wheel 122 which has knurled outer edges 123 and which is rotatable about a shaft 124 that has each of its ends mounted to the first arm 46 of the trident housing 40. The wheel 122 includes a spool or drum 126 (shown in phantom) having a smaller diameter than the diameter of the outer edges 123 of the wheel 122 and to which the proximal end 64 of the pull wire 60 is attached and around which the pull wire 60 is wound and unwound by rotation of the wheel 122 with the thumb of a hand.

When the wheel 122 is rotated in a clockwise direction, the pull wire 60 winds around the drum 126 of the wheel 122 which in turn causes a tension to be exerted on the pull wire 60 by the wheel 122 to pull and thereby bend the flexible tip portion 14 of the tubular body 12 in a rearward direction toward the trident housing 40.

Then, when the wheel 122 is rotated in a counter-clockwise direction, the pull wire 60 unwinds from the drum 126 of the wheel 122 in order to permit the flexible tip portion 14 of the tubular body 12 to return to its normal, straight configuration shown in FIG. 2.

Another embodiment of the present invention is illustrated in FIG. 7. Here the trident housing 40 has a threaded cap assembly 130 for manipulating the pull wire 60. The threaded cap assembly 130 is mounted to the second arm 48 of the trident housing 40. A Luer connector 56 is mounted to the first arm 46 of the trident housing 40. A proximal end 132 of the second arm 48 of the trident housing 40 is threaded with threads 133 so that the threads 133 of the second arm 48 of the trident housing 40 mesh with threads 134 on an inner surface 136 of a cap member 138 of the assembly 130.

The cap member 138 includes a ball bearing assembly 140 which includes an inner race 142 and an outer race 144 and ball bearings 146 therebetween. The ball bearing assembly 140 is slidably received into a shoulder 150 which is journaled into the proximal end 132 of the second arm 48 of the trident housing 40 and is movable with the cap member 138 relative to the proximal end 132 of the second arm 48 when the cap member 138 is rotated about and relative to the proximal end 132 of the second arm 48. The proximal end 64 of the pull wire 60 is connected to a washer 152 which is freely mounted between a surface 154 of the cap member 138 and the inner race 142 of the ball bearing assembly 140.

When the cap member 138 is rotated in a clockwise direction, the ball bearing assembly 140 moves rearwardly together with the cap member 138 relative to the trident housing 40 so that the washer 152 also moves rearwardly so as to pull the wire 60 and cause the flexible tip portion 14 of the tubular body 12 to bend toward the proximal end 20 of the tubular body 12. It will be appreciated that according to the teachings of the present invention, since the washer 152 is freely mounted between the surface 154 of the cap member 138 and the inner race 142 of the ball bearing assembly 140, the washer 152 is non-rotable relative to the cap member 138 when the cap member 138 is rotated so that the pull wire 60 is not twisted by the rotating action of the cap member 138.

It is apparent that one of the advantages of the curving tip catheter 10 of the present invention is that the curving tip catheter 10 can be manipulated with one hand, i.e., the pull wire 60 can be manipulated by the ratchet assembly 70, the lever assembly 100, the wheel assembly 120, or the threaded cap assembly 130 with the thumb of a hand, and the catheter 10 can be rotated with the same hand in order to direct the flexible tip portion 14 of the curving tip catheter 10 into a selected vessel branch of a network of branching blood vessels.

Further, since the flexible tip portion 14 of the tubular body 12 always curves with the first elongate passageway 23 toward the innermost radius of the curving flexible tip portion 14, the orientation of the curved flexible tip portion 14 is always known to the operator of the catheter 10. He will always know the position and direction of the curving flexible tip portion 14.

Also, the first and second metal bands 22 and 72 respectively, can be utilized as radio-opaque markers to further aid the operator of the curving tip catheter 10 in locating the curving flexible tip portion 14 of the curving tip catheter 10 within the branching network of blood vessels within the body for positioning the flexible tip portion 14 of the tubular body 12 at a desired location within a blood vessel.

From the foregoing description it is apparent that the curving tip catheter 10 of the present invention has a number of advantages, some of which have been described above and others of which are inherent in the invention. Also modifications can be made to the curving tip catheter 10 without departing from the teachings of the present invention. Accordingly, the scope of the invention is only to be limited as necessitated by the accompanying claims.

I claim:

1. A catheter adapted to be inserted into and through the lumen of a blood vessel in a network of branching blood vessels of a body and which is manipulatable therethrough to a desired blood vessel branch within the network of branching blood vessels, said catheter comprising: an elongate tubular body having a distal end and a proximat end; a flexible non-metallic tubular tip portion located at said distal end of said elongate tubular body; a metallic band mounted on said tip portion; at least first and second non-coaxial elongate passageways within said tubular body; at least first and second elongate lumens within said flexible tip portion and mating with said first and second respective elongate passageway within said tubular body; means associated with aid tubular body for providing torsional stiffness to said tubular body; mechanical means situated within said first passageway and said first lumen and coupled to said flexible tip portion for flexing said flexible tip portion; and means for introducing or withdrawing a fluid material into or from said second passageway in said tubular body whereby said catheter can be guided by said flexible tip portion through a branching network of blood vessels in a body to a site in the body for delivering a fluid or withdrawing a fluid from the site in the body, and said mechanical means for flexing said tip portion comprising a wire having a distal end soldered to said metallic band.

2. The catheter of claim 1 wherein the diameter of said first elongate passageway is equal to the diameter of said first elongate lumen.

3. The catheter of claim 1 wherein the diameter of said second elongate passageway is equal to the diameter of said second elongate lumen.

4. The catheter of claim 2 wherein said diameter of said first elongate passageway and said first elongate lumen is smaller than said diameter of said second elongate passageway and said second elongate lumen.

5. The catheter of claim 1 wherein said means associated with said tubular body for providing torsional stiffness to said tubular body is a sheath of braided wire positioned around said tubular body.

6. The catheter of claim 1 wherein said means associated with said tubular body for providing torsional stiffness to said tubular body is an inner plastic tubular lining within said tubular body and situated between said tubular body and said first and second elongate passageways.

7. The catheter of claim 1 including a Y-shaped housing member coupled to said proximal end of said catheter tubular body, and wherein said means for flexing said flexible tip portion and said means for introducing or withdrawing a fluid material into said second passageway in said tubular body are mounted to said Y-shaped housing, said Y-shaped housing having a leg portion into which said proximal end of said tubular body is inserted, and first and second arm positions.

8. The catheter of claim 7 wherein said means for flexing said flexible tip portion includes a ratchet assembly mounted to said first arm of said Y-shaped housing, said ratchet assembly comprising a spring biased pin which is slidable transversely of the axis of said pin through an elongate opening in said first arm of said Y-shaped housing, said pin including a washer having a plurality of stepped portions, two racks mounted within said first arm on each side of said elongate opening, extending parallel to the axis of said first arm portion, and having stepped portions thereon engagable with said stepped portions on said washer, said wire being connected to said pin so that when said plurality of stepped portions of said washer are disengaged from said plurality of stepped portions of said two racks and said pin moved transversely of the axis thereof within said elongate opening in said first arm and in a direction away from said tubular body, said wire pulls said flexible tip portion so that said flexible tip portion bends in a direction towards said Y-shaped housing, said flexible tip portion being straightened when said pin is moved in a direction towards said tubular body, and said engaging stepped portions serving to hold said pin a desired position.

9. The catheter of claim 7 wherein said means for flexing said flexible tip portion is a lever assembly mounted to said first arm of said Y-shaped housing, said lever assembly comprising an L-shaped lever which includes a first arm formed at a right angle relative to a second arm and an elbow therebetween, said first arm being pivotable about a shaft mounted to said first arm of said Y-shaped housing, said second arm of said lever being slidably received within an elongate opening in said first arm of said Y-shaped housing when said lever is pivoted about said shaft in a forward direction relative said tubular body, and said wire being attached to said elbow of said lever whereby when said lever is moved in a forward direction relative said tubular body, said wire pulls said flexible tip portion so that said flexible tip portion is bent in a direction toward said Y-shaped housing, and said flexible tip portion being straightened when said lever is moved in a rearward direction relative said tubular body.

10. The catheter of claim 7 wherein said means for flexing said flexible tip portion is a wheel assembly mounted to said first arm of said Y-shaped housing, said wheel assembly comprising a wheel mounted to a shaft within said first arm, said wheel including a drum having a diameter less than the diameter of said wheel, said wire being attached to said drum whereby when said wheel is rotated in one direction, said wire is wound around said drum to pull said wire in order to bend said flexible tip portion in a direction toward said Y-shaped housing and said flexible tip portion being straightened when said wheel is rotated in the opposite direction.

11. The catheter of claim 7 wherein said means for introducing or withdrawing a fluid material into said second passageway is mounted to said second arm of said Y-shaped housing.

12. The catheter of claim 7 wherein said means for flexing said flexible tip portion includes a threaded cap assembly mounted to said second arm of said Y-shaped housing, said threaded cap assembly comprising a threaded cap member and a floating washer to which said pull wire is connected and which is positioned between said cap member and the proximal end of said second arm, said cap member threadably engaging a threaded end portion of the proximal end of said second arm of said Y-shaped housing so that when said cap member is rotated in a counterclockwise direction, said washer is moved rearwardly relative to said second arm and said pull wire is pulled thereby to bend said flexible tip portion in a direction toward said Y-shaped housing, and said flexible tip portion being straightened when said cap member is rotated in a clockwise direction toward said Y-shaped housing.

13. The catheter of claim 12 wherein said means for introducing or withdrawing a fluid material into said second passageway is located in said first arm of said Y-shaped housing.

14. The catheter of claim 11 wherein said means for introducing or withdrawing a fluid material into said second passageway includes a Luer connector.

15. The catheter of claim 13 wherein said means for introducing or withdrawing a fluid material into said second passageway includes a Luer connector.

16. The catheter of claim 12 wherein said threaded cap assembly includes a ball bearing having an outer race fixed within said cap member and an inner race loosely received in said proximal end portion of said second arm and said floating washer is positioned to engage the rearwardly facing annular edge of said inner race on rotation of said cap member.

17. The catheter of claim 1 wherein said means for introducing or withdrawing a fluid material into or from said second passageway of said tubular body includes an opening in the distal end of said flexible tip portion, which communicates with said second lumen of said flexible tip portion and said second passageway of said tubular body.

18. The catheter of claim 5 wherein said first metallic band is radio-opaque.

19. The catheter of claim 4 wherein said diameter of said first elongate passageway and of said first elongate lumen is ½ the diameter of said diameter of said second elongate passageway and said second elongate lumen.

* * * * *